United States Patent [19]

Kelly et al.

[11] Patent Number: 5,637,255
[45] Date of Patent: Jun. 10, 1997

[54] CHIRAL DIOXOLANES

[75] Inventors: Stephen Kelly, Möhlin; Martin Schadt, Seltisberg, both of Switzerland

[73] Assignee: Rolic AG, Basel, Switzerland

[21] Appl. No.: 646,894

[22] Filed: Jan. 28, 1991

[30] Foreign Application Priority Data

Feb. 6, 1990 [CH] Switzerland ............... 371/90
Oct. 19, 1990 [CH] Switzerland ............... 3344/90

[51] Int. Cl.[6] .................................... C09K 19/34
[52] U.S. Cl. ........................................ 252/299.61
[58] Field of Search .............. 252/299.61, 299.62, 252/299.63; 549/430, 448

[56] References Cited

U.S. PATENT DOCUMENTS 4,873,019 10/1989 Krause et al. .............. 252/299.61
4,966,726 10/1990 Scherowsky et al. .......... 252/299.6

FOREIGN PATENT DOCUMENTS 234437 9/1987 European Pat. Off. ..
288813 11/1988 European Pat. Off. ..

OTHER PUBLICATIONS

Derwent A 89 E14 G06 L03 U11 ((1984).

Primary Examiner—C. H. Kelly
Attorney, Agent, or Firm—George W. Johnston; John P. Parise; Mark E. Waddell

[57] ABSTRACT

Chiral dopants of the formula

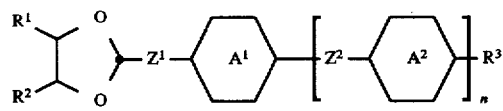

in which n represents the number 0 or 1; $R^3$ denotes a group of the general formula

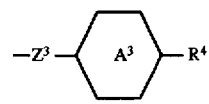

II or

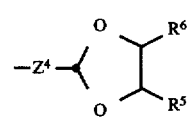

III $A^1$, $A^2$ and $A^3$, independently of one another, represent 1,4-phenylene which is unsubstituted or substituted by halogen, cyano and/or methyl and in which 1 or 2 CH groups may be replaced by nitrogen, or represent trans-1,4-cyclohexylene, trans-1,3-dioxane-2,5-diyl or naphthalene-2, 6-diyl, and ring $A^2$ additionally represents 1,4-biphenylene; $Z^1$ and $Z^4$, independently of one another, denote a single covalent bond or —$CH_2CH_2$—; $Z^2$ and $Z^3$, independently of one another, denote a single covalent bond, —$CH_2CH_2$—, —COO—, —OOC—, —$CH_2O$—, —$OCH_2$—, —C≡C—, —$(CH_2)_4$—, —$(CH_2)_3O$—, —$O(CH_2)_3$— or the trans-form of —CH=CH—$CH_2CH_2$—, —$CH_2CH_2$—CH=CH—, —CH=CH—$CH_2$—O— or —O—$CH_2$—CH=CH—; with the proviso that, if $R^3$ denotes a group of the formula II, at least one of the groups $Z^2$ and $Z^3$ denotes —$(CH_2)_4$—, —$(CH_2)_3$—O—, —O—$(CH_2)_3$— or the trans-form of —CH=CH—$CH_2$—$CH_2$—, —$CH_2$—$CH_2$—CH=CH—, —CH=CH—$CH_2$—O— or —O—$CH_2$—CH=CH—; $R^1$, $R^5$ and $R^6$ denote hydrogen, alkyl, phenyl or alkoxycarbonyl; $R^2$ denotes alkyl, phenyl or alkoxycarbonyl; $R^4$ denotes halogen, cyano, trifluoromethyl, trifluoromethoxy or alkyl in which one —$CH_2$—$CH_2$— may be replaced by —CH=CH— and/or one or two non-adjacent methylene groups may be replaced by —O—, —COO— and/or —OOC— and/or one methylene group methylene group may be replaced by —CHX—; X denotes halogen, cyano or methyl; and the dioxolane ring shown in the formula I is in optically active form, liquid-crystalline mixtures which contain such dopants, and their use for optical and electrooptical purposes.

17 Claims, No Drawings

CHIRAL DIOXOLANES

BACKGROUND OF THE INVENTION

1. Field of the Invention

The present invention relates to novel chiral dopants for liquid crystals, and to liquid-crystalline mixtures which contain such dopants, and to their use for optical and electrooptical purposes.

2. Description of the Invention

Liquid-crystal materials for electrooptical display devices frequently contain one or more optically active additives for inducing a chiral structure. For example, a nematic liquid crystal is preferably doped with an optically active additive for use in display devices having a twisted nematic structure, for example in order to avoid reverse twist in TN (twisted nematic) cells or in order to achieve adequate twisting in cells having a highly twisted nematic structure, such as STN (supertwisted nematic) cells, SBE (super birefringence effect) cells or OMI (optical mode interference) cells. Furthermore, cholesteric liquid crystals for phase-change cells can preferably comprise a nematic base material and one or more optically active dopants, and ferroelectric liquid crystals for display devices based on chiral, tilted, smectic phases can preferably comprise a material having a tilted smectic phase and one or more optically active dopants.

The electrooptical response curves of liquid-crystal display devices are temperature dependent, which is particularly disadvantageous when operated in multiplex mode. However, it is known that this temperature dependence can be compensated, at least partially, by adding a chiral dopant which induces a pitch which decreases with increasing temperature. An inverse temperature dependence of this type has only been found for a few compounds. However, it can also be achieved by using at least two chiral dopants which have different relative temperature dependences and induce different twist directions (DE-A-2827471 corresponding to U.S. Pat. No. 4 264 148). However, this usually requires a relatively high proportion of chiral dopants.

Cholesteric liquid crystals reflect light in a wavelength range for which the wavelength is approximately equal to the helix pitch. The spectral width of the reflected light can be varied by a suitable choice of the liquid crystal. The reflected light is fully circular-polarised. The direction of rotation of the reflected light depends on the direction of rotation of the cholesteric helical structure. The light circular-polarised in the opposite direction is transmitted without absorption. These properties can be utilized to produce optical filters, polarizers, analyzers etc. Furthermore, cholesteric liquid crystals have also occasionally be used for thermochromic applications and in cosmetic preparations.

Cholesteric liquid crystals for the above applications can preferably comprise a nematic or cholesteric base material and one or more chiral dopants, which allows the desired helix pitch to be established.

In order to achieve cholesteric mixtures having a pitch in the range of the wavelength of visible light, the chiral dopants should have high a helical twisting power and be readily soluble in customary liquid-crystal materials. In addition, the chiral dopants should have adequate stability, be readily compatible with the mesophase type of liquid-crystal material and should not restrict the mesophase range excessively. Such properties are also desirable for chiral dopants for achieving the twisted nematic structures mentioned at the outset, since their proportion could be kept so low that the properties of the liquid-crystal material are affected only insignificantly.

SUMMARY OF THE INVENTION

The invention relates to optically active compounds of the formula

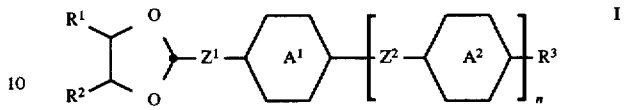

in which n represents the number 0 or 1; $R^3$ denotes a group of the formula

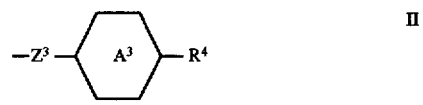

or

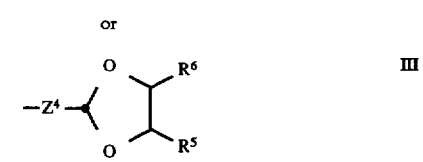

the rings $A^1$, $A^2$ and $A^3$, independently of one another, represent 1,4-phenylene which is unsubstituted or substituted by halogen, cyano and/or methyl and in which 1 or 2 CH groups may be replaced by nitrogen, or represent trans-1,4-cyclohexylene, trans-1,3-dioxane-2,5-diyl or naphthalene-2,6-diyl, and ring $A^2$ additionally represents 1,4-biphenylene; $Z^1$ and $Z^4$, independently of one another, denote a single covalent bond or —$CH_2CH_2$—; $Z^2$ and $Z^3$, independently of one another, denote a single covalent bond, —$CH_2CH_2$—, —COO—, —OOC—, —$CH_2O$—, —$OCH_2$—, —C≡C—, —$(CH_2)_4$—, —$(CH_2)_3O$—, —$O(CH_2)3$- or the trans-form of —CH=CH—$CH_2CH_2$—, —$CH_2CH_2$—CH=CH—, —CH=CH—$CH_2$—O— or —O—$CH_2$—CH=CH—; with the proviso that, if $R^3$ denotes a group of the formula II, at least one of the groups $Z^2$ and $Z^3$ denotes —$(CH_2)_4$—, —$(CH_2)_3$—O—, —O—$(CH_2)_3$— or the trans-form of —CH=CH—$CH_2$—$CH_2$—, —$CH_2$—$CH_2$—CH=CH—, —CH=CH—$CH_2$—O— or —O—$CH_2$—CH=CH—; $R^1$, $R^5$ and $R^6$ denote hydrogen, alkyl, phenyl or alkoxycarbonyl; $R^2$ denotes alkyl, phenyl or alkoxycarbonyl; $R^4$ denotes halogen, cyano, trifluoromethyl, trifluoromethoxy or alkyl in which one —$CH_2$—$CH_2$— may be replaced by —CH=CH— and/or one or two non-adjacent methylene groups may be replaced by —O—, —COO— and/or —OOC— and/or one methylene group may be replaced by —CHX—; X denotes halogen, cyano or methyl; and the dioxolane ring shown in the formula I is in optically active form.

The compounds of the formula I are very readily soluble in customary liquid-crystal materials and facilitate very high twisting of the liquid-crystal structure. In contrast to known materials having a high helical twisting power, the clearing points of liquid crystals are, in addition, generally only decreased insignificantly, or not at all, when compounds of the formula I are added. Some of the compounds according to the invention even have liquid-crystalline properties themselves. The compounds of the formula I are easy to prepare, have relatively low viscosity and are adequately stable to electrical and magnetic fields. They therefore meet the above mentioned requirements in an optimum manner.

DETAILED DESCRIPTION OF THE INVENTION

The invention concerns optically active compounds of the formula

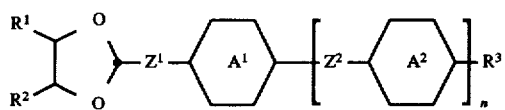

in which n is the number 0 or 1; $R^3$ is a group of the formula

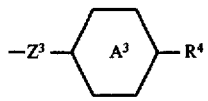

or

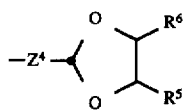

the rings $A^1$, $A^2$ and $A^3$, independently of one another, represent 1,4-phenylene which is unsubstituted or substituted with at least one of halogen, cyano or methyl and in which 1 or 2 CH groups may be replaced by nitrogen, or represent trans-1,4-cyclohexylene, trans-1,3-dioxane-2,5-diyl or naphthalene-2,6-diyl, and ring $A^2$ additionally is 1,4-biphenylene; $Z^1$ and $Z^4$, independently of one another, are a single covalent bond or —CH$_2$CH$_2$—; $Z^2$ and $Z^3$, independently of one another, are a single covalent bond, —CH$_2$CH$_2$—, —COO—, —OOC—, —CH$_2$O—, —OCH$_2$—, —C≡C—, —(CH$_2$)$_4$—, —(CH$_2$)$_3$O—, —O(CH$_2$)$_3$— or the trans-form of —CH=CH—CH$_2$CH$_2$—, —CH$_2$CH$_2$—CH=CH—, —CH=CH—CH$_2$—O— or —O—CH$_2$—CH=CH—; with the proviso that, if $R^3$ is a group of formula II, at least one of the groups $Z^2$ and $Z^3$ is —(CH$_2$)$_4$—, —(CH$_2$)$_3$—O—, —O—(CH$_2$)$_3$— or the trans-form of —CH=CH—CH$_2$—CH$_2$—, —CH$_2$—CH$_2$—CH=CH—, —CH=CH—CH$_2$—O— or —O—CH$_2$—CH=CH—; $R^1$, $R^5$ and $R^6$ each are hydrogen, alkyl, phenyl or alkoxycarbonyl; $R^2$ denotes alkyl, phenyl or alkoxycarbonyl; $R^4$ denotes halogen, cyano, trifluoromethyl, trifluoromethoxy or alkyl in which one —CH$_2$—CH$_2$— may be replaced by —CH=CH— and/or one or two non-adjacent methylene groups may be replaced by —O—, —COO— and/or —OOC— and/or one methylene group may be replaced by —CHX—; X denotes halogen, cyano or methyl; and the dioxolane ring shown in the formula I is in optically active form.

The compounds of the formula I are very readily soluble in customary liquid-crystal materials and facilitate very high twisting of the liquid-crystal structure. In contrast to known materials having a high helical twisting power, the clearing points of liquid crystals are, in addition, generally only decreased insignificantly, or not at all, when compounds of the formula I are added. Some of the compounds according to the invention even have liquid-crystalline properties themselves. The compounds of the formula I are easy to prepare, have relatively low viscosity and are adequately stable to electrical and magnetic fields.

The properties of the compounds of the formula I may be varied within broad ranges, depending on the number and meaning of the rings and substituents. For example, aromatic rings result in higher values of the optical anisotropy and saturated rings result in lower values. An increase in the clearing point can be achieved, for example, by introducing a further ring. Polar end groups, such as cyano, halogen, trifluoromethyl or trifluoromethoxy, and rings such as pyrimidine-2,5-diyl or trans-1,3-dioxane-2,5-diyl increase the dielectric anisotropy; rings such as 2,3-dicyano-1,4-phenylene reduce the dielectric anisotropy; and lateral halogen and cyano substituents contribute towards the dielectric constant both parallel and perpendicular to the longitudinal molecular axis, which, depending on the substitution pattern, can be utilized to increase or reduce the dielectric anisotropy. Furthermore, lateral substituents on one or more rings can often be used to substantially suppress any tendency towards formation of highly ordered smectic phases and often also to improve the solubility. Moreover, a C=C double bond in the side chain can be used to further modify the elastic properties, the threshold voltages, the addressing times, the mesophases, etc.

The present invention therefore additionally facilitates, in addition to the induction of high twist, the optimization of liquid-crystalline and electrooptical properties in a broad range, depending on the application and the desired properties.

For the purposes of the present invention, the term "halogen" denotes fluorine, chlorine, bromine or iodine, especially fluorine or chlorine. The term "1,4-phenylene which is unsubstituted or substituted with at least one of halogen, cyano or methyl and in which 1 or 2 CH groups may be replaced by nitrogen" encompasses groups such as 1,4-phenylene, 2-fluoro-1,4-phenylene, 2,3-difluoro-1,4-phenylene, 2-chloro-1,4-phenylene, 2-bromo-1,4-phenylene, 2-cyano-1,4-phenylene, 2,3-dicyano-1,4-phenylene, 2-methyl-1,4-phenylene, pyridine-2,5-diyl, pyrazine-2,5-diyl, pyrimidine-2,5-diyl and the like. Preferred groups are 1,4-phenylene, 2-fluoro-1,4-phenylene, 2,3-difluoro-1,4-phenylene, pyridine-2,5-diyl and pyrimidine-2,5-diyl.

The term "alkyl" denotes straight-chain and branched, optionally chiral groups having 1 to 12 carbon atoms, such as methyl, ethyl, propyl, isopropyl, butyl, isobutyl, 2-butyl (=1-methylpropyl), 2-methylbutyl, pentyl, hexyl, heptyl, octyl, 2-octyl (=1-methylheptyl), nonyl, decyl, undecyl, dodecyl and the like. Preferred alkyl radicals in $R^1$, $R^2$, $R^5$ and $R^6$ are $C_1$-$C_5$-alkyl radicals, in particular methyl.

The term "alkoxycarbonyl" denotes straight-chain and branched, optionally chiral groups such as methoxycarbonyl, ethoxycarbonyl, propoxycarbonyl, isopropoxycarbonyl, butyloxycarbonyl, isobutyloxycarbonyl, (2-butyl)oxycarbonyl, (2-methylbutyl)- oxycarbonyl, pentyloxycarbonyl, hexyloxycarbonyl and the like. Preferred alkoxycarbonyl radicals in $R^1$, $R^2$, $R^5$ and $R^6$ are the $C_2$-$C_7$-alkoxycarbonyl radicals, in particular the $C_2$-$C_5$-alkoxycarbonyl radicals.

The term "alkyl in which one —CH$_2$—CH$_2$— may be replaced by —CH=CH— and/or one or two non-adjacent methylene groups may be replaced by —O—, —COO— and/or —OOC— and/or one methylene group may be replaced by —CHX—" covers straight-chain and branched (optionally chiral) radicals such as alkyl, 1E-alkenyl, 3E-alkenyl, 4-alkenyl, alkenyl containing a terminal double bond, alkoxy, 2E-alkenyloxy, 3-alkenyloxy, alkenyloxy containing a terminal double bond, alkoxyalkyl, alkenyloxyalkyl, alkoxycarbonyl, alkoxycarbonylalkoxy (for example 1-(alkoxycarbonyl)-1-ethoxy), alkoxycarbonylalkoxycarbonyl (for example (1-alkoxycarbonyl)-1-ethoxycarbonyl), alkanoyloxy, 1-haloalkyl, 2-haloalkyl, 2-haloalkoxy, 2-haloalkoxycarbonyl, 1-cyanoalkyl, 2-cyanoalkyl, 2-cyanoalkoxy, 2-cyanoalkoxycarbonyl, 1-methylalkyl, 2-methylalkyl, 1-methylalkoxy, 2-methylalkoxy, 2-methylalkoxycarbonyl and the like. Examples of preferred radicals are methyl, ethyl, propyl, butyl, pentyl, hexyl, heptyl, octyl, nonyl, decyl, undecyl, dodecyl, 1-methylpropyl, 1-methylheptyl, 2-methylbutyl, 3-methylpentyl, vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4Z-heptenyl, 5-hexenyl, 6-heptenyl, 7-octenyl, 8-nonenyl, 9-decenyl, 10-undecenyl, 11-dodecenyl, methoxy, ethoxy, propoxy, butyloxy, pentyloxy, hexyloxy, heptyloxy, octyloxy, nonyloxy, decyloxy, undecyloxy, dodecyloxy, 1-methylpropoxy, 1-methylheptyloxy, 2-methylbutyloxy, 3-methylpentyloxy, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, methoxymethyl, ethoxymethyl, propoxymethyl, allyloxymethyl, methoxycarbonyl, ethoxycarbonyl, propoxycarbonyl, 1-methylpropoxycarbonyl, 1-(methoxycarbonyl) ethoxy, 1-(ethoxycarbonyl)ethoxy, 1-(methoxycarbonyl)ethoxycarbonyl, 1-(ethoxycarbonyl) ethoxycarbonyl, 1-(isopropoxycarbonyl)ethoxycarbonyl, 1-(butyloxycarbonyl)ethoxycarbonyl, acetoxy, propionyloxy, butyryloxy, 1-fluoropropyl, 1-fluoropentyl, 1-chloropropyl, 2-fluoropropyl, 2-fluoropentyl, 2-chloropropyl, 2-fluoropropoxy, 2-fluorobutyloxy, 2-fluoropentyloxy, 2-fluorohexyloxy, 2-chloropropoxy, 2-chlorobutyloxy, 2-fluoropropoxycarbonyl, 2-fluorobutyloxycarbonyl, 2-fluoropentyloxycarbonyl, 2-fluoro-3-methylbutyloxycarbonyl, 2-fluoro-4-methylpentyloxycarbonyl, 2-chloropropoxy-carbonyl, 1-cyanopropyl, 1-cyanopentyl, 2-cyanopropyl, 2-cyanopentyl, 2-cyanopropoxy, 2-cyanobutyloxy, 2-cyanopentyloxy, 2-cyanohexyloxy, 2-cyanopropoxycarbonyl, 2-cyanobutyloxycarbonyl, 2-cyano-3-methylbutyloxycarbonyl, 2-cyano-4-methylpentyloxycarbonyl and the like.

Formula I covers optically active compounds of the formulae below

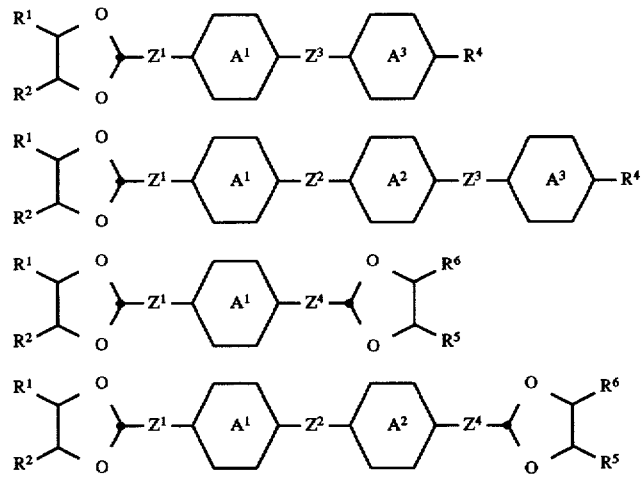

in which $R^1$, $R^2$, $R^4$, $R^5$, $R^6$, $A^1$, $A^2$, $A^3$, $Z^1$, $Z^2$, $Z^3$ and $Z^4$ are each as defined above, with the proviso that, in the compounds of the formulae I-1 and I-2, at least one of the groups $Z^2$ and $Z^3$ denotes —(CH$_2$)$_4$—, —(CH$_2$)$_3$—O—, —O—(CH$_2$)$_3$— or the trans-form of —CH=CH—CH$_2$—CH$_2$—, —CH$_2$—CH$_2$—CH=CH—, —CH=CH—CH$_2$—O— or —O—CH$_2$—CH=CH—.

The compounds of the formulae I-3 and I-4 are chiral dopants having a particularly high helical twisting power.

The compounds of the formula I contain at least one optically active dioxolane ring. The dioxolane ring shown in the formula I has a chiral carbon atom in position 4 (i.e. adjacent to $R^2$) and, if $R^1$ is not hydrogen, a further chiral carbon atom in position 5 (i.e. adjacent to $R^1$). It is obvious to a person skilled in the art that, in order to achieve optical activity, the carbon atom in position 4 of the dioxolane ring must completely or predominantly be in R- or S-form and, if $R^1$ and $R^2$ are identical, that the carbon atom in position 5 of the dioxolane ring should completely or predominantly have the same configuration as the carbon atom in position 4 or in principle may also have a R/S ratio of 50:50. In order to achieve the highest possible helical twisting power, the carbon atom in position 4 of the dioxolane ring should preferably have the a very high optical purity in the R- or S-configuration and, if $R^1$ is not hydrogen, that the carbon atom in position 5 of the dioxolane ring should preferably have a very high optical purity in that configuration which increases the helical twisting power. Preferred optical isomers having high helical twisting power are the (4R)-isomers and the (4S)-isomers of the compounds of the formula I in which $R^1$ is hydrogen, and the (4R,5R)-isomers and the (4S,5S)-isomers of the compounds of the formula I in which $R^1$ denotes alkyl, phenyl or alkoxycarbonyl.

In general, particularly preferred compounds are those of the formulae I, I-1 and I-2 in which $A^1$, $A^2$ and $A^3$, independently of one another, represent 1,4-phenylene which is unsubstituted or substituted by halogen, cyano and/or methyl (in particular 1,4-phenylene, 2-fluoro-1,4-phenylene or 2,3-difluoro-1,4-phenylene) or represent trans-1,4-cyclohexylene, or one of the groups $A^1$, $A^2$ and $A^3$ also represents pyrimidine-2,5-diyl, and furthermore one of the groups $Z^2$ and $Z^3$ denotes —(CH$_2$)$_4$—, —O—(CH$_2$)$_3$—, —(CH$_2$)$_3$—O— or the trans-form of —CH$_2$—CH$_2$—CH=CH—, —CH=CH—CH$_2$—CH$_2$—, —O—CH$_2$—CH=CH— or —CH=CH—CH$_2$—O—, and, if present, the other of the groups $Z^2$ and $Z^3$ denotes a single covalent bond.

These compounds are very stable and in general particularly readily accessible from known precursors of liquid crystals.

Very particularly preferred compounds are those of the formulae I-3 and F4 in which the rings $A^1$ and $A^2$, independently of one another, represent 1,4-phenylene which is unsubstituted or substituted by halogen, cyano and/or methyl (in particular 1,4-phenylene, 2-fluoro-1,4-phenylene or 2,3-difluoro-1,4-phenylene) or represent trans-1,4-cyclohexylene, or the ring $A^2$ also represents pyrimidine-2, 5-diyl or 4,4'-biphenylene, and furthermore a group $Z^2$, if present, denotes a single covalent bond, —CH$_2$—CH$_2$—, —COO— or —OOC— (in particular a single covalent bond).

However, since the helical twisting power of the compounds according to the invention is determined principally by the optically active dioxolane ring, one or more of these particularly preferred rings and bridging groups may be replaced by the other rings mentioned in the formula I for A$^1$, A$^2$ and A$^3$ and the bridging groups mentioned for Z$^1$, Z$^2$, Z$^3$ and Z$^4$ in order to obtain a similar effect and likewise good compatibility with customary liquid crystals. However, preferred compounds of the formulae I and I-1 to I-4 are those in which in each case one of the rings A$^1$, A$^2$ and A$^3$ represents 1,4-phenylene which is unsubstituted or substituted by halogen, cyano and/or methyl, or represents pyridine-2,5-diyl, pyrimidine-2,5-diyl, trans-1,4-cyclohexylene, trans-1,3-dioxane-2,5-diyl or naphthalene-2,6-diyl, and the ring A$^2$ additionally represents 4,4'-biphenylene, the others of the rings A$^1$, A$^2$ and A$^3$ (if present), independently of one another, represent 1,4-phenylene which is unsubstituted or substituted by halogen, cyano and/or methyl (in particular unsubstituted 1,4-phenylene) or represent trans-1,4-cyclohexylene, one of the groups Z$^2$ and Z$^3$ denotes a single covalent bond, —CH$_2$CH$_2$—, —COO—, —OOC—, —CH$_2$O—, —OCH$_2$—, —C≡C—, —(CH$_2$)$_4$—, —(CH$_2$)$_3$O—, —O(CH$_2$)$_3$— or the trans-form of —CH=CH—CH$_2$CH$_2$—, —CH$_2$CH$_2$—CH=CH—, —CH=CH—CH$_2$—O— or —O—CH$_2$—CH=CH—, and the other of the groups Z$^2$ and Z$^3$ (if present) denotes a single covalent bond, with the proviso that, if R$^3$ denotes a group of the formula III, at least one of the groups Z$^2$ and Z$^3$ denotes —(CH$_2$)$_4$—, —(CH$_2$)$_3$—O—, —O—(CH$_2$)$_3$— or the trans-form of —CH=CH—CH$_2$—CH$_2$—, —CH$_2$—CH$_2$—CH=CH—, —CH=CH—CH$_2$—O— or —O—CH$_2$—CH=CH—.

Examples of particularly preferred compounds of the formula I are the optically active compounds of the formulae below

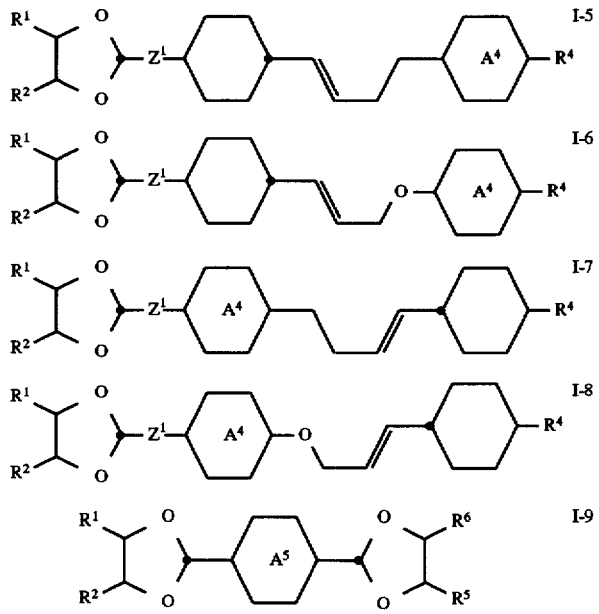

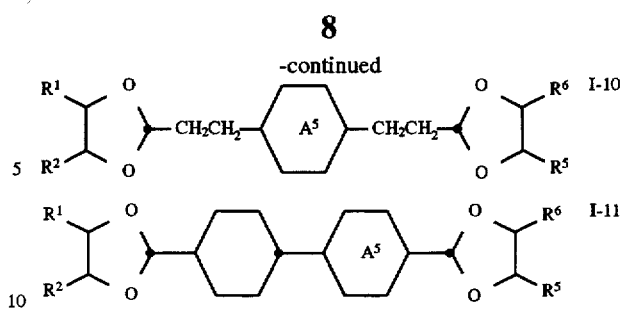

in which R$^1$, R$^2$, R$^4$, R$^5$ and R$^6$ are as defined above, and the rings A$^4$ and A$^5$ each are 1,4-phenylene which is unsubstituted or substituted with at least one of halogen, cyano or methyl (preferably 1,4-phenylene, 2-fluoro-1,4-phenylene or 2,3-difluoro-1,4-phenylene) or trans-1,4-cyclohexylene, and ring A$^5$ additionally is 4,4'-biphenylene.

In the above formulae I, I-1, I-2 and I-5 to I-8, R$^4$ in each case preferably is halogen (in particular fluorine or chlorine), cyano, trifluoromethyl, trifluoromethoxy, alkyl, alkenyl, alkoxy or alkenyloxy. In an alkyl radical R$^4$, however, one or two non-adjacent methylene groups may, if desired, be replaced by —O—, —COO— and/or —OOC—, and/or one methylene group may be replaced by —CHX— (in which X denotes halogen, cyano or methyl). This possibility can be utilized, for example, to increase the helical twisting power by introducing chiral groups starting from simple, optically active compounds.

Preferred examples of such groups are the radicals derived from optically active lactic acid, such as 1-(alkoxycarbonyl)ethoxy and 1-(alkoxycarbonyl)ethoxycarbonyl. In the above formulae, R$^4$ may therefore also preferably in each case denote one of these radicals.

Preferably, R$^4$ has 1 to 18 carbon atoms. R$^4$ radicals having 1 to 12 carbon atoms, in particular those having 1 to 7 carbon atoms, are preferred.

Very particularly preferred compounds of the formula I in which R$^3$ is a group of the formula III are the compounds of the formulae

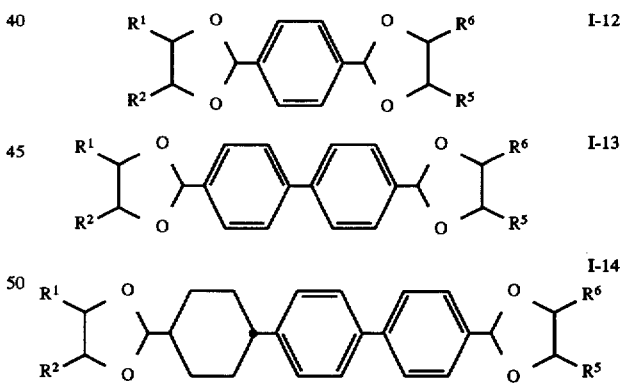

in which R$^1$, R$^2$, R$^5$ and R$^6$ are as defined above.

The compounds of the formula I may furthermore contain an end group of the formula III, i.e. a further dioxolane ring. This group may be optically inactive, but preferred groups of the formula III are those which are present in an optically active form which increases the helical twisting power. Compounds having an increased helical twisting power which are particularly easy to prepare are those in which the two dioxolane rings have the same configuration and contain the same rings. In the formula III, R$^5$ may therefore preferably have the same meaning and the same configuration at the adjacent carbon atom as R$^1$, and R$^6$ may preferably have the same meaning and the same configuration at the adjacent carbon atom as $R^2$. This also applies analogously to the two dioxolane radicals in the formulae I-3, I-4, I-12, I-13 and I-14.

Preferred optical isomers are thus the compounds having the relative configuration indicated in the formula below:

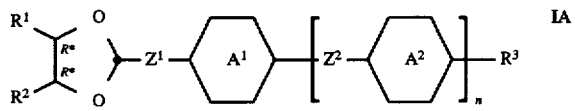

in which $R^3$ denotes a group of the formula

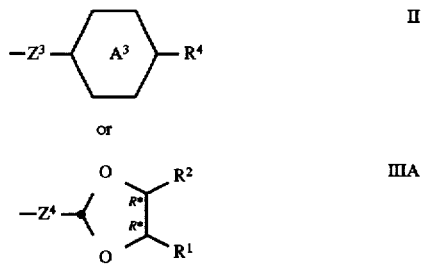

$n$, $A^1$, $A^2$, $A^3$, $Z^1$, $Z^2$, $Z^3$, $Z^4$, $R^1$, $R^2$ and $R^4$ are as defined above, with the proviso that, if $R^3$ is a group of the formula II, at least one of the groups $Z^2$ and $Z^3$ is —(CH$_2$)$_4$—, —(CH$_2$)$_3$—O—, —O—(CH$_2$)$_3$— or the trans-form of —CH=CH—CH$_2$—CH$_2$—, —CH$_2$—CH$_2$—CH=CH—, —CH—CH—CH$_2$—O— or —O—CH$_2$—CH=CH—; and the asymmetric carbon atoms labelled R* are all in the R-configuration or are all in the S-configuration.

The formula IA covers the optical isomers indicated with R and the optical antipodes thereof which have the same helical twisting power, but the opposite twist direction.

Preferred optically active compounds of the formula IA are those in which $R^1$ and $R^2$ are preferably different or identical and denote $C_2$-$C_7$-alkoxycarbonyl, in particular $C_2$-$C_5$-alkoxycarbonyl. These compounds are readily accessible from the corresponding optically active tartaric acids or dialkyl tartrates. Particularly preferred compounds are those of the formulae I-1 to I-14 in which in each case $R^1$ and $R^2$ are different or preferably identical and denote $C_2$-$C_7$-alkoxycarbonyl (in particular $C_2$-$C_5$-alkoxycarbonyl), $R^5$ is as defined for $R^1$, $R^6$ is as defined for $R^2$, and the asymmetric carbon atoms have the relative configuration indicated in formula IA.

Further preferred optically active compounds of the formula IA are those in which $R^2$ denotes methyl or phenyl and $R^1$ is as defined for $R^2$ or denotes hydrogen. These compounds are readily accessible from the corresponding optically active diols, namely 2,3-butanediol, 1,2-diphenyl-1,2-ethanediol, 1,2-propanediol or 1-phenyl-1,2-ethanediol. Particularly preferred compounds are those of the formulae I-1 to I-14 in which in each case $R^2$ denotes methyl or phenyl, $R^1$ is as defined for $R^2$ or denotes hydrogen, $R^5$ is as defined for $R^1$, $R^6$ is as defined for $R^2$, and the asymmetric carbon atoms have the relative configuration indicated in the formula IA.

In the above formula IA and in the subgroups of compounds of the formula I mentioned above as being preferred, rings $A^1$, $A^2$, $A^3$, $A^4$ and $A^5$, $Z^1$, $Z^2$, $Z^3$ and $Z^4$ may in each case in particular have the preferred meanings indicated in connection with the formulae I and I-1 to 1-14, with the proviso that, if $R^3$ denotes a group of the formula II, at least one of the groups $Z^2$ and $Z^3$ denotes —(CH$_2$)$_4$—, —(CH$_2$)$_3$—O—, —O—(CH$_2$)$_3$— or the trans-form of —CH=CH—CH$_2$—CH$_2$—, —CH$_2$—CH$_2$—CH=CH—, —CH=CH—CH$_2$—O— or —O—CH$_2$—CH=CH—.

The compounds according to the invention may be prepared, for example, by reacting an aldehyde of the formula OHC—$Z^1$—$A^1$—($Z^2$—$A^2$)n—$R^3$ or an acetal thereof with an optically active diol of the formula $R^1$—CH(OH)—CH(OH)—$R^2$. The reaction of the aldehyde or of a suitable acetal (for example dimethyl acetal) with the diol may be carried out in a manner known per se. The reaction is expediently carried out in an inert organic solvent (for example an aromatic hydrocarbon, such as benzene, toluene or xylene) in the presence of a catalytic amount of an organic or inorganic acid, such as p-toluenesulphonic acid, sulphuric acid or dry hydrogen chloride. The temperature and pressure are not crudal, but the reaction is preferably carried out at the reflux temperature (with separation of the water formed) and at atmospheric pressure.

If present, a second dioxolane ring (if $R^3$ denotes a group of the formula III) may be formed analogously, likewise from an aldehyde (or acetal) and a diol. If the two diols [$R^1$—CH(OH)—CH(OH)—$R^2$ and $R^5$—CH(OH)—CH(OH)—$R^6$] are identical, the two dioxolane rings may, if desired, be formed in one step.

If the compound of the formula I contains one or more ester groups in $Z^2$, $Z^3$ and/or $R^4$, the esterification concerned may preferably also be delayed until after formation of the dioxolane ring. If desired, the introduction of ether groups and other functional groups may also be delayed until after formation of the dioxolane ring.

Methods of this type are known to those skilled in the art, for example from the preparation of liquid-crystalline dioxanes. The diols required for the preparation are known or analogues of known compounds. The aldehydes required as starting materials are likewise known compounds or can be prepared by methods known per se. Such compounds and methods are disclosed, for example, in U.S. Pat. No. 4 573 005, EP-A-0113459 and EP-A-0106991 (corresponding to GB-E 106991).

The invention also relates to a liquid-crystalline mixture containing at least one liquid-crystalline base material and at least one optically active compound of formula L Suitable base materials are in principle all conventional liquid-crystal materials which have a twistable liquid-crystal phase having an adequate mesophase range. The compounds of the formula I are particularly suitable as chiral dopants for nematic or cholesteric base materials. The liquid-crystalline base material may be an individual compound or a mixture and preferably has a clearing point of at least about 60° C.

The proportion of chiral dopant of the formula I is essentially determined by its helical twisting power and by the desired pitch. The proportion of the chiral dopant can therefore vary within a broad range depending on the application and can be, for example, from about 0.1 to 30% by weight. For display devices based on liquid crystals having a twisted nematic structure, a pitch of from about 3 to about 40 μm is usually necessary, depending on the cell type and thickness, and a correspondingly small proportion is therefore sufficient. By contrast, applications based on the reflection of visible light by cholesteric layers necessitate pitches of less than 2 μm, for example from about 0.4 to about 0.6 μm, which requires a correspondingly higher proportion of chiral dopant.

A large number of suitable liquid-crystalline base materials are known and are commercially available. In general, liquid-crystalline mixtures containing 2 or more components are preferred as base materials. In principle, however, it is also possible to use one liquid-crystalline compound as the base material if it has a sufficiently broad mesophase.

Particularly suitable components for liquid-crystalline base materials are compounds of the formulae below

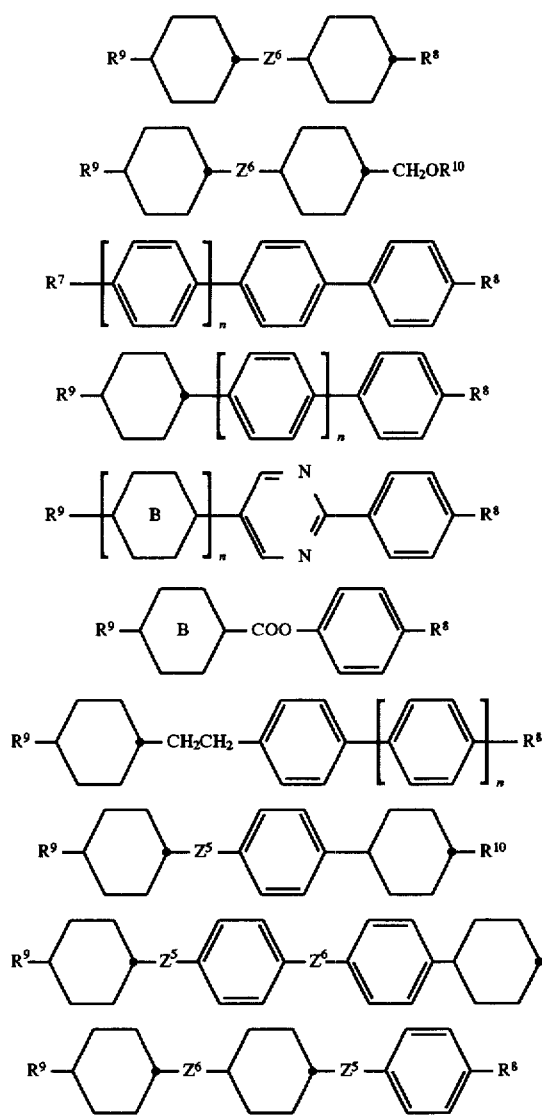

in which n represents the number 0 or 1; $R^7$ denotes alkyl, alkoxy, alkenyl or alkenyloxy; $R^8$ denotes cyano, alkyl, alkoxy, alkenyl or alkenyloxy; $R^9$ and $R^{10}$, independently of one another, denote alkyl or alkenyl; ring B represents 1,4-phenylene or trans-1,4-cyclohexylene; $Z^5$ denotes a single covalent bond, —COO— or —CH$_2$CH$_2$—; and $Z^6$ denotes a single covalent bond or —CH$_2$CH$_2$—.

$R^7$, $R^8$, $R^9$ and $R^{10}$ preferably contain a maximum of 12 carbon atoms each, particularly preferably a maximum of 7 carbon atoms each. Preferred alkenyl groups are 1E-alkenyl, 3E-alkenyl and 4Z-alkenyl. Preferred alkenyloxy groups are 2E-alkenyloxy and 3Z-alkenyloxy.

The invention is illustrated in greater detail by means of the examples below. In connection with liquid-crystal phases and phase transitions, C denotes a crystalline phase, $S_B$ denotes a smectic B phase, N denotes a nematic phase, N* denotes a cholesteric phase and I denotes the isotropic phase. p denotes the helix pitch, and λmax denotes the wavelength of the selectively reflected, circular-polarised light. Optical antipodes have in each case "mirror-image properties", i.e. the same melting points, etc., but result in an opposite direction of rotation of the helix and the opposite circular-polarisation of reflected light. Unless indicated otherwise, (such as by use of present tense verbs) the Examples were carried out as written.

EXAMPLE 1

A solution of 0.8 g of 4-[(E)-3-(trans-4-pentylcyclohexyl) allyloxy]benzaldehyde and 1.0 g of dimethyl L(+)-tartrate in 50 ml of toluene was treated with 2 drops of 10% (vol.) sulphuric acid. The mixture was boiled for 2.5 hours, the water formed being simultaneously removed by distillation. 4 drops of triethylamine were then added to the reaction mixture. The mixture was cooled and washed with 20 ml of 1 N sodium bicarbonate solution and twice with 20 ml of water in each case, dried over sodium sulphate, filtered and evaporated. Chromatography of the residue on silica gel using toluene/ethyl acetate (1:1 by volume) and recrystallisation from ethanol gave pure dimethyl (4R,5R)-2-(4-[(E)-3-(trans-4-pentylcyclohexyl)allyloxy]phenyl-1,3-dioxolane-4,5-dicarboxylate, m.p. 70° C.

The following compounds can be prepared in an analogous manner:

diethyl (4R,5R)-2-(4-[(E)-3-(trans-4-pentylcydohexyl) allyloxy]phenyl)-1,3-dioxolane-4,5-dicarboxylate, m.p. 55° C.;

diisopropyl (4R,5R)-2-(4-[(E)-3-(trans-4-pentylcyclohexyl)allyloxy]phenyl)-1,3-dioxolane-4,5-dicarboxylate, m.p. 51° C.;

diisobutyl (4R,5R)-2-(4-[(E)-3-(trans-4-pentylcyclohexyl)allyloxy]phenyl)-1,3-dioxolane-4,5-dicarboxylate;

dimethyl (4R,5R)-2-(4-[3-(trans-4-pentylcyclohexyl)-1-propoxy]phenyl)-1,3-dioxolane-4,5-dicarboxylate, m.p. 66° C.;

diethyl (4R,5R)-2-(4-[3-(trans-4-pentylcydohexyl)-1-propoxy]phenyl)-1,3-dioxolane-4,5-dicarboxylate, m.p. 57° C.;

diisopropyl (4R,5R)-2-(4-[3-(trans-4-pentylcyclohexyl)-1-propoxy]phenyl)-1,3-dioxolane-4,5-dicarboxylate, m.p. 52° C.;

dibutyl (4R,5R)-2-(4-[3-(trans-4-pentylcydohexyl)-1-propoxy]phenyl)-1,3-dioxolane-4,5-dicarboxylate, m.p. 42° C.;

dimethyl (4R,5R)-2-(4-[4-(trans-4-pentylcyclohexyl)-1-butyl]phenyl)-1,3-dioxolane-4,5-dicarboxylate;

diethyl (4R, 5R)-2-(4-[4-(trans-4-pentylcydohexyl)-1-butyl]phenyl)-1,3-dioxolane-4,5-dicarboxylate;

diisopropyl (4R,5R)-2-(4-[4-(trans-4-pentylcydohexyl)-1-butyl]phenyl)-1,3-dioxolane-4,5-dicarboxylate;

dibutyl (4R,5R)-2-(4-[4-(trans-4-pentylcyclohexyl)-1-butyl]phenyl)-1,3-dioxolane-4,5-dicarboxylate;

dimethyl (4R,5R)-2-(4-[(E)-(trans-4-pentylcyclohexyl)-3-butenyl]phenyl)-1,3-dioxolane-4,5-dicarboxylate;

diethyl (4R,5R)-2-(4-[(E)-(trans-4-pentylcyclohexyl)-3-butenyl]phenyl)-1,3-dioxolane-4,5-dicarboxylate;

diisopropyl (4R,5R)-2-(4-[(E)-(trans-4-pentylcydohexyl) -3-butenyl]phenyl)-1,3-dioxolane-4,5-dicarboxylate;

dibutyl (4R,5R)-2-(4-[(E)-(trans-4-pentylcydohexyl)-3-butenyl]phenyl)-1,3-dioxolane-4,5-dicarboxylate;

dimethyl (4R,5R)-2-(4-[(E)-3-(trans-4-propylcyclohexyl) allyloxy]phenyl)-1,3-dioxolane-4,5-dicarboxylate;

diethyl (4R,5R)-2-(4-[(E)-3-(trans-4-propylcyclohexyl) allyloxy]phenyl)-1,3-dioxolane-4,5-dicarboxylate;

diisopropyl (4R,5R)-2-(4-[(E)-3-(trans-4-propylcydohexyl)allyloxy]phenyl)-1,3-dioxolane-4,5-dicarboxylate;

diisobutyl (4R,5R)-2-(4-[(E)-3-(trans4-propylcyclohexyl) allyloxy]phenyl)-1,3-dioxolane-4,5-dicarboxylate;

dimethyl (4R,5R)-2-(4-[3-(trans-4-propylcyclohexyl)-1-propoxy]phenyl)-1,3-dioxolane-4,5-dicarboxylate;

diethyl (4R,5R)-2-(4-[3-(trans-4-propylcyclohexyl)-1-propoxy]phenyl)-1,3-dioxolane-4,5-dicarboxylate;

diisopropyl (4R,5R)-2-(4-[3-(trans-4-propylcydohexyl)-1-propoxy]phenyl)-1,3-dioxolane-4,5-dicarboxylate;

dibutyl (4R,5R)-2-(4-[3-(trans-4-propylcyclohexyl)-1-propoxy]phenyl)-1,3-dioxolane-4,5-dicarboxylate;

dimethyl (4R,5R)-2-(4-[4-(trans-4-propylcyclohexyl)-1-butyl]phenyl)-1,3-dioxolane-4,5-dicarboxylate;

diethyl (4R,5R)-2-(4-[4-(trans-4-propylcyclohexyl)-1-butyl]phenyl)-1,3-dioxolane-4,5-dicarboxylate;

diisopropyl (4R,5R)-2-(4-[4-(trans-4-propylcydohexyl)-1-butyl]phenyl)-1,3-dioxolane-4,5-dicarboxylate;

dibutyl (4R,5R)-2-(4-[4-(trans-4-propylcydohexyl)-1-butyl]phenyl)-1,3-dioxolane-4,5-dicarboxylate;

dimethyl (4R,5R)-2-(4-[(E)-(trans-4-propylcyclohexyl)-3-butenyl]phenyl)-1,3-dioxolane-4,5-dicarboxylate;

diethyl (4R,5R)-2-(4-[(E)-(trans-4-propylcyclohexyl)-3-butenyl]phenyl)-1,3-dioxolane-4,5-dicarboxylate;

diisopropyl (4R,5R)-2-(4-[(E)-(trans-4-propylcydohexyl)-3-butenyl]phenyl)-1,3-dioxolane-4,5-dicarboxylate;

dibutyl (4R,5R)-2-(4-[(E)-(trans-4-propylcyclohexyl)-3-butenyl]phenyl)-1,3-dioxolane-4,5-dicarboxylate;

4-[(4R,5R)-4,5-dimethoxycarbonyl-1,3-dioxolan-2-yl]-4'-[(E)-3-(trans-4-pentylcyclohexyl) allyloxy]biphenyl;

4-[(4R,5R)-4,5-diethoxycarbonyl-1,3-dioxolan-2-yl]-4'-[(E)-3-(trans-4-pentylcyclohexyl) allyloxy]biphenyl;

4-[(4R,5R)-4,5-diisopropoxycarbonyl-1,3-dioxolan-2-yl]-4'-[(E)-3-(trans-4-pentylcyclohexyl) allyloxy]biphenyl;

4-[(4R,5R)-4,5-diisobutyloxycarbonyl-1,3-dioxolan-2-yl]-4'-[(E)-3-(trans-4-pentylcydohexyl) allyloxy]biphenyl;

4-[(4R,5R)-4,5-dimethoxycarbonyl-1,3-dioxolan-2-yl]-4'-[4-(trans-4-pentylcydohexyl)-1-propoxy]diphenyl;

4-[(4R,5R)-4,5-diethoxycarbonyl-1,3-dioxolan-2-yl]-4'-[4-(trans-4-pentylcydohexyl)-1-propoxy]diphenyl;

4-[(4R,5R)-4,5-diisopropoxycarbonyl-1,3-dioxolan-2-yl]-4'-[4-(trans-4-pentylcydohexyl)-1-propoxy]diphenyl;

4-[(4R,5R)-4,5-dibutyloxycarbonyl-1,3-dioxolan-2-yl]-4'-[4-(trans-4-pentylcyclohexyl)-1-propoxy]diphenyl;

5 4-[(4R,5R)-4,5-dimethoxycarbonyl-1,3-dioxolan-2-yl]-4'-[4-(trans-4-pentylcyclohexyl)-1-butyl]biphenyl;

4-[(4R,5R)-4,5-diethoxycarbonyl-1,3-dioxolan-2-yl]-4'-[4-(trans-4-pentylcydohexyl)-1-butyl]biphenyl;

4-[(4R,5R)-4,5-diisopropoxycarbonyl-1,3-dioxolan-2-yl]-4'- [4-(trans-4-pentylcydohexyl)-1-butyl]biphenyl;

4-[(4R,5R)-4,5-dibutyloxycarbonyl-1,3-dioxolan-2-yl]-4'-[4-(trans-4-pentylcydohexyl)-1-butyl]biphenyl;

4-[(4R,5R)-4,5-dimethoxycarbonyl-1,3-dioxolan-2-yl]-4'-[(E)-3-(trans-4-pentylcyclohexyl) butenyl]diphenyl;

4-[(4R,5R)-4,5-diethoxycarbonyl-1,3-dioxolan-2-yl]-4'-[(E)-3-(trans-4-pentylcyclohexyl) butenyl]diphenyl;

4-[(4R,5R)-4,5-diisopropoxycarbonyl-1,3-dioxolan-2-yl]-4'-[(E)-3-(trans-4-pentylcyclohexyl) butenyl]diphenyl;

4-[(4R,5R)-4,5-dibutyloxycarbonyl-1,3-dioxolan-2-yl]-4'-[(E)-3-(trans-4-pentylcyclohexyl) butenyl]diphenyl;

4-[(4R,5R)-4,5-dimethoxycarbonyl-1,3-dioxolan-2-yl]-4'-[(E)-3-(trans-4-propylcydohexyl) allyloxy]biphenyl;

4-[(4R,5R)4,5-diethoxycarbonyl-1,3-dioxolan-2-yl]-4'-[(E)-3-(trans-4-propylcydohexyl) allyloxy]biphenyl;

4-[(4R,5R)-4,5-diisopropoxycarbonyl-1,3-dioxolan-2-yl]-4'-[(E)-3-(trans-4-propylcydohexyl) allyloxy]biphenyl;

4-[(4R,5R)-4,5-diisobutyloxycarbonyl-1,3-dioxolan-2-yl]-4'-[(E)-3-(trans-4-propylcyclohexyl) allyloxy]biphenyl;

4-[(4R,5R)-4,5-dimethoxycarbonyl-1,3-dioxolan-2-yl]-4'-[4-(trans-4-propylcydohexyl)-1-propoxy]diphenyl;

4-[(4R,5R)-4,5-diethoxycarbonyl-1,3-dioxolan-2-yl]4'-[4-(trans-4-propylcydohexyl)-1-propoxy]diphenyl;

4-[(4R,5R)-4,5-diisopropoxycarbonyl-1,3-dioxolan-2-yl]-4'-[4-(trans-4-propylcydohexyl)-1-propoxy]diphenyl;

4-[(4R,5R)-4,5-dibutyloxycarbonyl-1,3-dioxolan-2-yl]-4'-[4-(trans-4-propylcydohexyl)-1-propoxy]diphenyl;

4-[(4R,5R)-4,5-dimethoxycarbonyl-1,3-dioxolan-2-yl]-4'-[4-(trans-4-propylcydohexyl)-1-butyl]biphenyl; 4-[(4R,5R)-4,5-diethoxycarbonyl-1,3-dioxolan-2-yl]-4'-[4-(trans-4-propylcydohexyl)-1-butyl]biphenyl;

4-[(4R,5R)-4,5-diisopropoxycarbonyl-1,3-dioxolan-2-yl]-4'- [4-(trans-4-propylcydohexyl)-1-butyl]biphenyl;

4-[(4R,5R)-4,5-dibutyloxycarbonyl-1,3-dioxolan-2-yl]-4'-[4-(trans-4-propylcydohexyl)-1-butyl]biphenyl;

4-[(4R,5R)-4,5-dimethoxycarbonyl-1,3-dioxolan-2-yl]-4'-[(E)-3-(trans-4-propylcyclohexyl) butenyl]diphenyl;

4-[(4R,5R)-4,5-diethoxycarbonyl-1,3-dioxolan-2-yl]-4'-[(E)-3-(trans-4-propylcyclohexyl) butenyl]diphenyl;

4-[(4R,5R)-4,5-diisopropoxycarbonyl-1,3-dioxolan-2-yl]-4'-[(E)-3-(trans-4-propylcyclohexyl) butenyl]diphenyl;

4-[(4R,5R)-4,5-dibutyloxycarbonyl-1,3-dioxolan-2-yl]-4'-[(E)-3-(trans-4-propylcyclohexyl) butenyl]diphenyl.

EXAMPLE 2

A solution of 1.0 g of terephthaldehyde, 5.8 g of dimethyl (R,R)-2,3-bis (trimethylsiloxy)succinate in 25 ml of ethylene chloride was treated at 0° C. under a nitrogen atmosphere with 0.14 ml of boron trifluoride ethyl etherate, the mixture was stirred for 15 minutes, 0.06 ml of trifluoromethanesulphonic add was added, the mixture was stirred at 0° C. for a further 30 minutes, and then at room temperature overnight. The mixture was cooled to 0° C., 25 ml of concentrated sodium carbonate solution were added dropwise, and the mixture was stirred at room temperature for a further 15 minutes. The organic phase was separated off, and the aqueous phase was then extracted twice with 25 ml of dichloromethane in each case. The combined organic phases were washed twice with 100 ml of water in each case, dried over magnesium sulphate, filtered and subsequently evaporated. The residue was purified by chromatography on silica gel using hexane/ ethyl acetate (1:1 by volume). Recrystallisation from a hexane/ethyl acetate mixture (1:1 by volume) gave pure dimethyl 2,2'-(4-phenylene)bis(4R, 5R)-1,3-dioxolane-4,5-dicarboxylate of m.p. (C-I) 88° C.

The dimethyl (R,R)-2,3-bis(trimethylsiloxy)succinate used as starting material was prepared as follows:

A solution of 20 g of dimethyl L(+)-tartaric add and 35 ml of triethylamine in 200 ml of toluene was treated dropwise at −5° C. and under a nitrogen atmosphere with 32 g of trimethylchlorosilane. A white reaction mixture formed, and was stirred at room temperature for a further 90 minutes. 100 ml of saturated sodium bicarbonate solution were added to the mixture, which was then extracted three times with 50 ml of ethyl acetate in each case. The combined organic phases were washed twice with 100 ml of saturated sodium bicarbonate solution in each case, dried over magnesium sulphate, filtered and then evaporated. Distillation of the residue gave 36 g of dimethyl (R,R)-2,3-bis(trimethylsiloxy)succinate, b.p. 123°–125° C./0.07 mm Hg.

The following compounds can be prepared in an analogous manner:

diethyl 2,2'-(4-phenylene)-bis(4R,5R)-1,3-dioxolane-4,5-dicarboxylate, m.p. 75° C.;

diisopropyl 2,2'-(4-phenylene)-bis(4R,5R)-1,3-dioxolane-4,5-dicarboxylate, m.p. 78° C.;

dibutyl 2,2'-(4-phenylene)-bis(4R,5R)-1,3-dioxolane-4,5-dicarboxylate, m.p. 41° C.;

dimethyl 2,2'-(4,4'-biphenylyl)-bis[(4R,5R)-1,3-dioxolane]-4,5-dicarboxylate, m.p. 133° C.;

diethyl 2,2'-(4,4'-biphenylyl)-bis[(4R,5R)-1,3-dioxolane]-4,5-dicarboxylate, m.p. 79° C.;

diisopropyl 2,2'-(4,4'-biphenylyl)-bis[(4R,5R)-1,3-dioxolane]-4,5-dicarboxylate, m.p. 97° C.;

dibutyl 2,2'-(4,4'-biphenylyl)-bis[(4R,5R)-1,3-dioxolane]-4,5-dicarboxylate, m.p. 67° C.

EXAMPLE 3

In order to measure the induced pitch and the temperature dependence thereof in liquid-crystal materials, the following liquid-crystal base mixture BM-1 was used:

| | | |
|---|---|---|
| 5.36% | by weight of | 4'-ethyl-4-cyanobiphenyl, |
| 3.18% | " | 4'-propyl-4-cyanobiphenyl, |
| 6.08% | " | 4'-butyl-4-cyanobiphenyl, |
| 6.53% | " | 4-(trans-4-propylcyclohexyl)benzonitrile, |
| 14.67% | " | 4-(trans-4-pentylcyclohexyl)benzonitrile, |
| 5.21% | " | 4-ethyl-1-(trans-4-propylcyclohexyl)benzene, |
| 16.54% | " | 4-ethoxy-1-[2-(trans-4-propylcyclohexyl)ethyl]benzene, |
| 5.60% | " | 4"-pentyl-4-cyano-p-terphenyl, |
| 5.71% | " | 4'-(trans-4-pentylcyclohexyl)-4-cyanobiphenyl, |
| 15.95% | " | 1-[2-(trans-4-butylcyclohexyl)ethyl]-4-(trans-4-pentylcyclohexyl)benzene, |
| 4.74% | " | 4-[2-(trans-4-butylcyclohexyl)ethyl]-4'-(trans-4-pentylcyclohexyl)biphenyl, |
| 7.59% | " | 4-[2-(trans-4-butylcyclohexyl)ethyl]-4'-(trans-4-pentylcyclohexyl)-1,1'-ethylenedibenzene, |
| 2.84% | " | 4-cyanophenyl trans-4-[2-(trans-4-propylcyclohexyl)ethyl]cyclohexanecarboxylate; | m.p. <−30° C., c.p. (N-I) 90° C.; Δε=8.5, Δn=0.139 and η=22 mPa·s, measured at 22° C.

One of the following optically active dopants was added in each case to the liquid-crystal base mixture BM-1:

D-1=dimethyl 2,2'-(4-phenyl)-bis(4R,5R)-1,3-dioxolane-4,5-dicarboxylate,

D-2=diisopropyl 2,2'-(4,4'-biphenyl)-bis(4R,5R)-1,3-dioxolane-4,5-dicarboxylate.

The results shown in Table 1 were obtained for the mixtures containing chiral dopants, A, B and C denoting the parameters of the expansion into a series $$\frac{1}{pc} = A + BT_1 + CT_1^2$$

and p, c and T1 have the following meanings:

T$_1$=T =22° C.

T=temperature in ° C.

p=pitch in μm (a positive value denotes a right-hand helical structure and a negative value denotes a left-hand helical structure)

c=concentration of the optically active dope in % by weight.

TABLE 1

| Mixture | Dopant | A [10$^{-2}$ · mm$^{-1}$ · % by wt.$^{-1}$] | B [10$^{-4}$ · mm$^{-1}$ · % by wt.$^{-1}$ · °C.$^{-1}$] | C [10$^{-6}$ · mm$^{-1}$ · % by wt.$^{-1}$ · °C.$^{-2}$] | p,c (at 22° C.) [mm. % by wt.] |
|---|---|---|---|---|---|
| M-1 | 1.0% by wt. of D-1 | −25.50 | −15.92 | 0.77 | −3.92 |
| M-2 | 1.0% by wt. of D-2 | −26.86 | 8.82 | −2.00 | −3.72 |

We claim:

1. An optically active compound of the formula

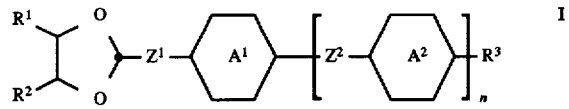

wherein n is the number 0 or 1; R$^3$ is a group of the formula

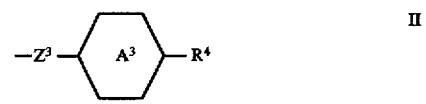

or

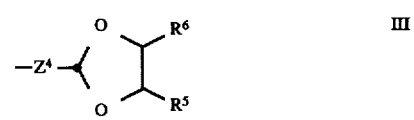

the rings A$^1$, A$^2$ and A$^3$, independently of one another, are 1,4-phenylene which is unsubstituted or substituted with halogen and in which 1 or 2 CH groups may be replaced by nitrogen, or represent trans-1,4-cyclohexylene, and ring A$^2$ additionally is 1,4-biphenylene; Z$^1$ and Z$^4$, independently of one another, are a single covalent bond or —CH$_2$CH$_2$—; Z$^2$ and Z$^3$, independently of one another, are a single covalent bond, —CH$_2$CH$_2$—, —C≡C—, —(CH$_2$)$_4$—, —(CH$_2$)$_3$O—, —O(CH$_2$)$_3$— or the trans-form of —CH=CH—CH$_2$CH=—, —CH$_2$—CH$_2$—CH=CH—, CH=CH—CH$_2$—O— or —O—CH$_2$—CH=CH—; with the proviso that, if R$^3$ is a group of formula II, at least one of the groups Z$^2$ and Z$^3$ is —(CH$_2$)$_4$—, —(CH$_2$)$_3$—O—, —O— (CH$_2$)$_3$—, or the trans-form of —CH=CH—CH$_2$—CH$_2$—, —CH$_2$—CH$_2$—CH=CH—, —CH=CH—CH$_2$—O— or —O—CH$_2$—CH=CH—; R$^1$, R$^5$ and R$^6$ each are alkyl of 1 to 12 carbon atoms, phenyl or alkoxycarbonyl of 2 to 7 carbon atoms; R$^2$ denotes alkyl of 1 to 12 carbon atoms, phenyl or alkoxycarbonyl of 2 to 7 carbon atoms; R$^4$ denotes halogen, cyano, trifluoromethyl, trifluoromethyoxy or an alkyl or alkenyl of 1 to 18 carbon atoms or in which one or two non-adjacent methylene groups may be replaced by —O—, —COO— or —OOC— or one methylene group may be replaced by —CHX—; X denotes halogen and the dioxolane ring shown in the formula I is in optically active form.

2. The optically active compound according to claim 1, having the relative configuration of the formula

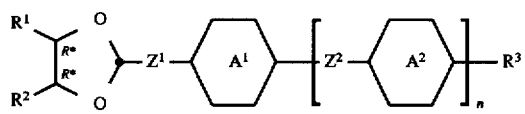   IA in which $R^3$ is a group of the formula

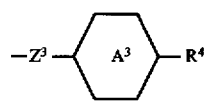   II or

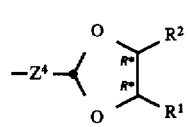   IIIA n, $A^1$, $A^2$, $A^3$, $Z^1$, $Z^2$, $Z^3$, $Z^4$, $R^1$, $R^2$ and $R^4$ are as defined in claim 1, with the proviso that, if $R^3$ is a group of the formula II, at least one of the groups $Z^2$ and $Z^3$ is —(CH$_2$)$_4$—, —(CH$_2$)$_3$—O—, —O—(CH$_2$)$_3$— or the trans-form of —CH=CH—CH$_2$—CH$_2$—, —CH$_2$—CH$_2$—CH=CH—, —CH=CH—CH$_2$—O— or —O—CH$_2$—CH=CH—; and the asymmetric carbon atoms labelled R* are all in the R-configuration or are all in the S-configuration.

3. The optically active compound according to claim 1, of the formula

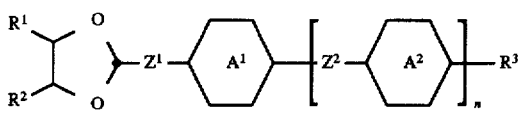   I in which $R^3$ is a group of the formula

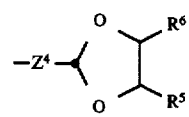   III $R^1$, $R^2$, $R^5$, $R^6$, n, $Z^1$, $Z^2$, $Z^4$, $A^1$ and $A^2$ are as defined in claim 1.

4. The optically active compound according to claim 2 of the formula

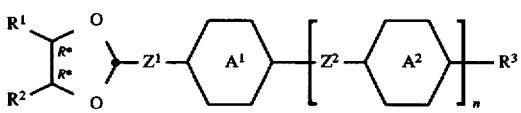   IA in which $R^3$ is a group of the formula

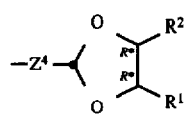   IIIA $R^1$, $R^2$, n, $Z^1$, $Z^2$, $Z^4$, $A^1$ and $A^2$ are as defined in claim 1.

5. The optically active compound according to claim 1, wherein one of the rings $A^1$, $A^2$ and $A^3$ is 1,4-phenylene which is unsubstituted or substituted with halogen, or is pyridine-2,5-diyl, pyrimidine-2,5-diyl, trans-1,4-cyclohexylene, and $A^2$ additionally is 4,4'-biphenylene, and the others of the rings $A^1$, $A^2$ and $A^3$, independently of one another, are 1,4-phenylene which is unsubstituted or substituted with at least one of halogen, or trans-1,4-cyclohexylene.

6. The optically active compound according to claim 5, wherein rings $A^1$, $A^2$ and $A^3$ independently of one another, are 1,4-phenylene which is unsubstituted or substituted with halogen, or is trans-1,4-cyclohexylene, or one of the groups $A^1$, $A^2$ and $A^3$ also is pyrimidine-2,5-diyl, one of the groups $Z^2$ and $Z^3$ is —(CH$_2$)$_4$—, —(CH$_2$)$_3$—O—, —O—(CH$_2$)$_3$— or the trans-form of —CH=CH—CH$_2$—CH$_2$—, —CH$_2$—CH$_2$—CH=CH—, —CH=CH—CH$_2$—O— or —O—CH$_2$—CH=CH—, and the other of the groups $Z^2$ and $Z^3$ is a single covalent bond.

7. The optically active compound according to claim 1, selected from the group of formulae consisting of:

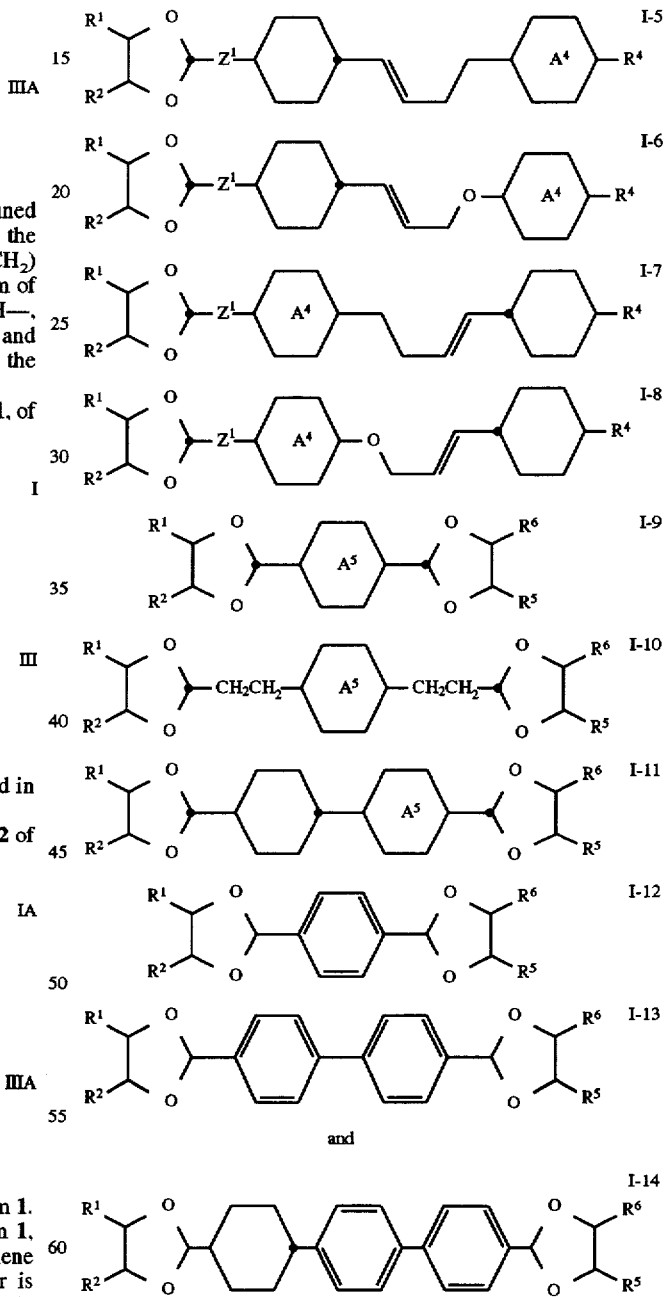

wherein $R^1$, $R^2$ and $R^4$ are as defined in claim 1; $R^5$ and $R^6$ are as defined in claim 1, rings $A^4$ and $A^5$ are 1,4-phenylene which is unsubstituted or substituted with halogen, or is trans-1,4-cyclohexylene, and ring $A^5$ additionally can be 4,4'-biphenylene.

8. The optically active compound according to claim 1, wherein $R^4$ is halogen, cyano, trifluoromethyl, trifluoromethoxy, alkyl, alkenyl, alkoxy, alkenyloxy, 1-(alkoxycarbonyl)ethoxy or 1-(alkoxycarbonyl) ethoxycarbonyl.

9. The optically active compound according to claim 7, wherein $R^4$ is halogen, cyano, trifluoromethyl, trifluoromethoxy, alkyl, alkenyl, alkoxy, alkenyloxy, 1-(alkoxycarbonyl)ethoxy or 1-(alkoxycarbonyl) ethoxycarbonyl.

10. The optically active compound according to claim 8, wherein $R^4$ has 1 to 12 carbon atoms.

11. The optically active compound according to claim 9, wherein $R^4$ has 1 to 7 carbon atoms.

12. The optically active compound according to claim 7, wherein $R^4$ has 1 to 12 carbon atoms.

13. The optically active compound according to claim 12, wherein $R^4$ has 1 to 7 carbon atoms.

14. The optically active compound according to claim 2, wherein $R^1$ and $R^2$ each are $C_2$-$C_7$-alkoxycarbonyl or $R^1$ and $R^2$ each are methyl or $R^1$ and $R^2$ each are phenyl or $R^1$ is hydrogen and $R^2$ is methyl or phenyl, $R^5$ is as defined for $R^1$, $R^6$ is as defined for $R^2$, and the asymmetric carbon atoms have the relative configuration indicated in claim 2.

15. The optically active compound according to claim 7, wherein $R^1$ and $R^2$ each are $C_2$-$C_7$-alkoxycarbonyl or $R^1$ and $R^2$ each are methyl or $R^1$ and $R^2$ each are phenyl or $R^1$ is hydrogen and $R^2$ is methyl or phenyl, $R^5$ is as defined for $R^1$, $R^6$ is as defined for $R^2$, and the asymmetric carbon atoms have the relative configuration indicated in claim 2.

16. A liquid-crystalline mixture comprising a liquid-crystalline base material having liquid crystalline properties and at least one optically active compound of the formula:

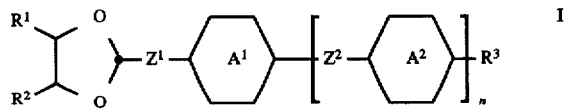

I wherein n is the number 0 or 1; $R^3$ is a group of the formula

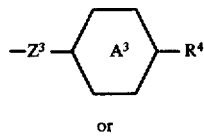

II or

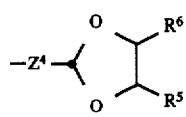

III the rings $A^1$, $A^2$ and $A^3$, independently of one another, are 1,4-phenylene which is unsubstituted or substituted with halogen and in which 1 or 2 CH groups may be replaced by nitrogen, or represent trans-1,4-cyclohexylene, and ring $A^2$ additionally is 1,4-biphenylene; $Z^1$ and $Z^4$, independently of one another, are a single covalent bond or —$CH_2CH_2$—; $Z^2$ and $Z^3$, independently of one another, are a single covalent bond, —$CH_2CH_2$—, —C≡C—, —$(CH_2)_4$—, —$(CH_2)_3$O—, —O$(CH_2)_3$— or the trans-form of —CH=CH—$CH_2CH_2$—, —$CH_2$—$CH_2$—CH=CH—, CH=CH—$CH_2$—O— or —O—$CH_2$—CH=CH—; with the proviso that, if $R^3$ is a group of formula II, at least one of the groups $Z^2$ and $Z^3$ is —$(CH_2)_4$—, —$(CH_2)_3$—O—, —O—$(CH_2)_3$—, or the trans-form of —CH=CH—$CH_2$—$CH_2$—, —$CH_2$—$CH_2$—CH=CH—, —CH=CH—$CH_2$—O— or —O—$CH_2$—CH=CH—; $R^1$, $R^5$ and $R^6$ each are alkyl of 1 to 12 carbon atoms, phenyl or alkoxycarbonyl of 2 to 7 carbon atoms; $R^2$ denotes alkyl of 1 to 12 carbon atoms, phenyl or alkoxycarbonyl of 2 to 7 carbon atoms; $R^4$ denotes halogen, cyano, trifluoromethyl, trifluoromethyoxy or an alkyl or alkenyl of 1 to 18 carbon atoms in which one or two non-adjacent methylene groups may be replaced by —O—, —COO— or —OOC— or one methylene group may be replaced by —CHX—; X denotes halogen and the dioxolane ring shown in the formula I is in optically active form.

17. An electro-optical cell comprising:

(a) two plate means;

(b) liquid crystal means including a liquid crystalline base material having liquid crystalline properties and an optically active dopant of the formula:

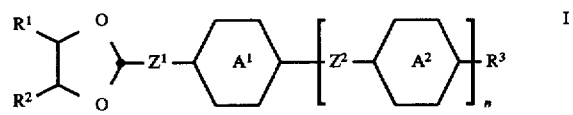

I wherein n is the number 0 or 1; $R^3$ is a group of the formula

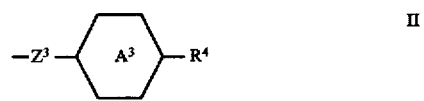

II or

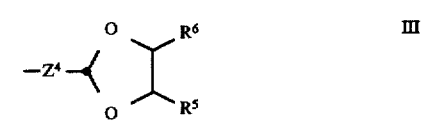

III the rings $A^1$, $A^2$ and $A^3$, independently of one another, are 1,4-phenylene which is unsubstituted or substituted with halogen and in which 1 or 2 CH groups may be replaced by nitrogen, or represent trans-1,4-cyclohexylene, and ring $A^2$ additionally is 1,4-biphenylene; $Z^1$ and $Z^4$, independently of one another, are a single covalent bond or —$CH_2CH_2$—; $Z^2$ and $Z^3$, independently of one another, are a single covalent bond, —$CH_2CH_2$—, —C≡C—, —$(CH_2)_4$—, —$(CH_2)_3$—, —O$(CH_2)_3$— or the trans-form of —CH=CH—$CH_2CH_2$—, —$CH_2$—$CH_2$—CH=CH—, CH=CH—$CH_2$—O— or —O—$CH_2$—CH=CH—; with the proviso that, if $R^3$ is a group of formula II, at least one of the groups $Z^2$ and $Z^3$ is —$(CH_2)_4$—, —$(CH_2)_3$—O—, —O—$(CH_2)_3$—, or the trans-form of —CH=CH—$CH_2$—$CH_2$—, —$CH_2$—$CH_2$—CH=CH—, —CH=CH—$CH_2$—O— or —O—$CH_2$—CH=CH—; $R^1$, $R^5$ and $R^6$ each are alkyl of 1 to 12 carbon atoms, phenyl or alkoxycarbonyl of 2 to 7 carbon atoms; $R^2$ denotes alkyl of 1 to 12 carbon atoms, phenyl or alkoxycarbonyl of 2 to 7 carbon atoms; $R^4$ denotes halogen, cyano, trifluoromethyl, trifluoromethyoxy or an alkyl or alkenyl of 1 to 18 carbon atoms in which one or two non-adjacent methylene groups may be replaced by —O—, —COO— or —OOC— or one methylene group may be replaced by —CHX—; X denotes halogen and the dioxolane ring shown in the formula I is in optically active form; and (c) means for applying an electric potential to the plate means.

* * * * *

UNITED STATES PATENT AND TRADEMARK OFFICE
CERTIFICATE OF CORRECTION

PATENT NO. : 5,637,255
DATED : June 10, 1997
INVENTOR(S) : Stephen Kelly and Martin Schadt It is certified that error appears in the above-indentified patent and that said Letters Patent is hereby corrected as shown below:

Column 16, claim 1, line 52, "$CH_2CH=$ —," change to -- $CH_2CH_2$-, --

Column 18, claim 6, line 2, "and$A^3$" change to -- and $A^3$, --

Column 20, claim 17, line 43, "$(CH_2)_4$-, -$(CH_2)_3$-," change to -- $(CH_2)_4$-, -$(CH_2)_3O$-, --

Signed and Sealed this

Sixteenth Day of September, 1997

Attest:

BRUCE LEHMAN

*Attesting Officer*  *Commissioner of Patents and Trademarks*